United States Patent [19]
Aziz

[11] 4,323,068
[45] Apr. 6, 1982

[54] DIAPER WITH EMBOSSED TEXTILE SHEET

[75] Inventor: Mohammed I. Aziz, Cincinnati, Ohio

[73] Assignee: The Procter & Gamble Company, Cincinnati, Ohio

[21] Appl. No.: 124,411

[22] Filed: Feb. 25, 1980

Related U.S. Application Data

[63] Continuation-in-part of Ser. No. 927,186, Jul. 24, 1978, abandoned.

[51] Int. Cl.³ .............................................. A41B 13/02
[52] U.S. Cl. .................................................... 128/287
[58] Field of Search ............ 128/284, 286, 287, 290 R

[56] References Cited

U.S. PATENT DOCUMENTS

| | | | |
|---|---|---|---|
| 2,964,441 | 12/1960 | Goldstone | 428/171 |
| 3,101,520 | 8/1963 | George et al. | 128/290 W |
| 3,616,157 | 10/1971 | Smith | 428/171 |
| 3,857,144 | 12/1974 | Bustin | 428/180 |
| 3,886,941 | 6/1971 | Duane et al. | 128/287 |
| 3,911,187 | 10/1975 | Paley | 428/180 |
| 3,929,135 | 12/1975 | Thompson | 128/287 |
| 4,041,951 | 8/1977 | Sanford | 128/290 W |

*Primary Examiner*—C. Fred Rosenbaum
*Attorney, Agent, or Firm*—John M. Pollaro; Fredrick H. Braun; Richard C. Witte

[57] ABSTRACT

An improvement in the embossing of a thermoplastic textile, in particular the topsheet of an absorbent structure such as a diaper, which improves the high load caliper of the textile. The knobs and depressions of the mated embossing rolls used to emboss the textile have side walls which define a small angle with respect to a radius of the embossing roll. The preferred embossing knobs and depressions each define a frustum with a rhombic base and land, with the longer diagonal of the rhombus aligned in the machine direction of the embossing roll. The resulting embossed textile has stronger bosses, and thus maintains a greater caliper under load, than is observed in the prior art embossed textile.

5 Claims, 13 Drawing Figures

PRIOR ART

DIAPER WITH EMBOSSED TEXTILE SHEET

This is a continuation of application Ser. No. 927,186, filed July 24, 1978 and now abandoned.

TECHNICAL FIELD

The field of the invention is the art of embossing, and more particularly the art of embossing a thermoplastic textile in order to increase its ability to isolate two surfaces between which it is placed under a moderate load. The primary use for the embossed material is as a topsheet for an absorbent structure, such as a diaper.

BACKGROUND ART

The most pertinent art of which the inventor is aware is U.S. Pat. No. 4,041,951, issued to Sanford on Aug. 16, 1977, and assigned to the owner of the present invention. The Sanford patent discloses that textile material may be embossed using mated steel embossing rolls in order to form a pattern of bosses which serves to isolate the skin of the wearer of an absorbent structure such as a diaper from the underlying absorbent material in order to improve the surface dryness of the absorbent structure. (As used herein, "textile" refers to a substantially planar sheet or web of a thermoplastic material including nonwoven and woven fabrics and films, as well as analogous materials. As a preferred embodiment of the invention, the Sanford patent discloses the use of a male steel embossing roll and a rubber-surfaced nip roll to emboss the material, wherein the knobs on the male roll are elliptical in cross section, having a land area of approximately 0.084 inches (2.13 mm.) by 0.042 inches (1.07 mm.) and a knob height of approximately 0.070 inches (1.78 mm.), said knobs being arranged in a diamond-shaped array containing six knobs per inch of roll width (0.236 knobs per mm.) and twelve rows of knobs per inch of roll circumference (0.472 knobs per mm.). The Sanford patent above cited is hereby incorporated herein by reference to more completely define the background and objects of the present invention.

DISCLOSURE OF INVENTION

The present invention defines an improvement over the Sanford disclosure by providing an embossed textile having a pattern of bosses which more effectively resists debossment as a result of pressure applied to the embossed textile when it is incorporated in an absorbent structure.

This is accomplished by embossing the textile with mated steel embossing rolls which have a knob and depression pattern with mating side walls which define a plane angle of less than about 28 degrees, and more preferably about 20 degrees, with respect to a plane which is perpendicular to a tangent plane of the embossing surface. This pattern results in a lower clearance between the adjacent side walls of a mating knob and depression when the rolls are separated by a given roll clearance as measured along a radius common to the mating rolls. This reduced side wall clearance is believed to enhance the degree of cold drawing of the textile during embossing as well as to provide sharper definition of the resulting boss than is observed in the prior art embossing technique.

DETAILED DESCRIPTION OF THE INVENTION

While the following disclosure provides a detailed description of one preferred embodiment of the invention in order to enable those skilled in the art to practice this invention, this description is not intended to limit the scope of the invention, which is defined in claims concluding this specification.

Figure 1:
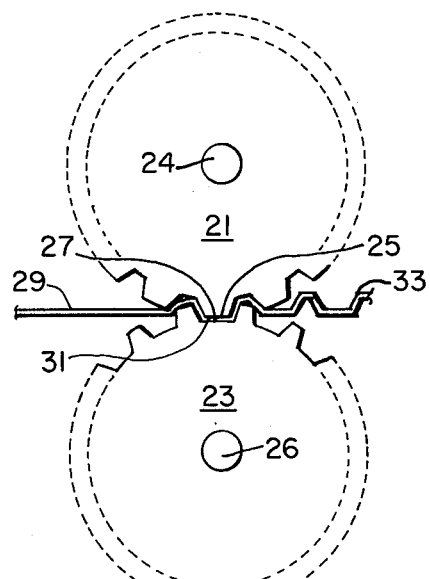
FIG. 1 is a schematic side elevational view of mating embossing rolls as they emboss a textile passed therebetween.

The essence of the process of embossing using mated steel embossing rolls is shown in FIG. 1, wherein male embossing roll 21 and female embossing roll 23 are aligned with their respective axes of rotation, 24 and 26, parallel and the knobs 25 of male embossing roll 21 closely approaching depressions 27 of female embossing roll 23, somewhat like the meshing of gears, at nip 31. Unembossed textile 29 is fed through the nip 31 between male embossing roll 21 and female embossing roll 23, and as a result the unembossed material 29 is transformed into embossed textile 33.

Figure 2:
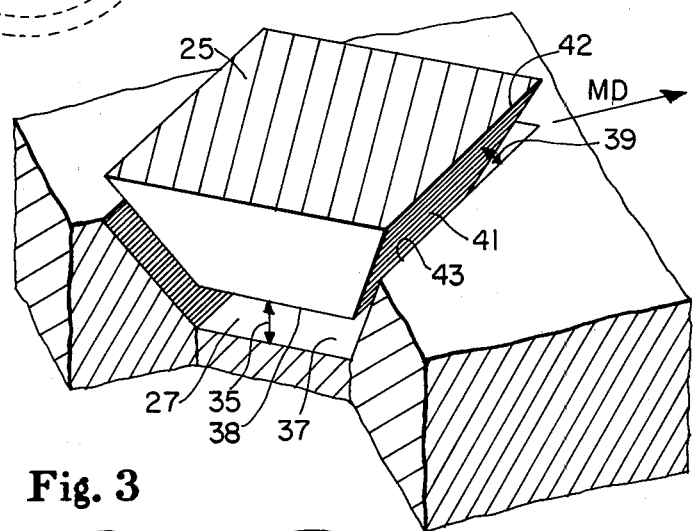
FIG. 2 is an enlarged perspective view of fragments of the male and female embossing rolls, showing a mating knob and depression of the embossing rolls in greater detail.

FIG. 2 shows, in greatly enlarged fashion, the juxtaposition of a knob 25 of the male embossing roll 21 and a depression 27 of female embossing roll 23. Double-headed schematic arrow 35 in FIG. 2 indicates the perpendicular distance between floor 37 of depression 27 and land 38 of knob 25 (hereinafter: roll clearance), while double-headed schematic arrow 39 defines the perpendicular clearance between side wall 41 of knob 25 and side wall 43 of depression 27 (hereinafter: side wall clearance). Knob 25 and its corresponding depression 27 are so aligned that at the point of their closest approach a radius of male embossing roll 21 passing perpendicularly through land 38 of knob 25 and a radius of female embossing roll 23 passing perpendicularly through floor 37 of depression 27 would be collinear. Thus, if the roll clearance 35 was reduced to zero, mating knob 25 and depression 27 would fit very nearly exactly together so that the surfaces of corresponding side walls such as side wall 41 of knob 25 and side wall 43 of depression 27 would be substantially coextensive and coplanar.

Figure 4:
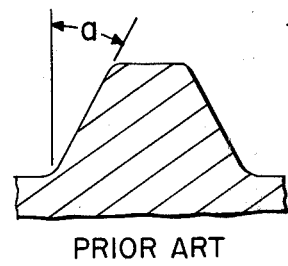
FIG. 4 is a sectional view of an embossing knob taken along line 4—4 of FIG. 3.
Figure 3:
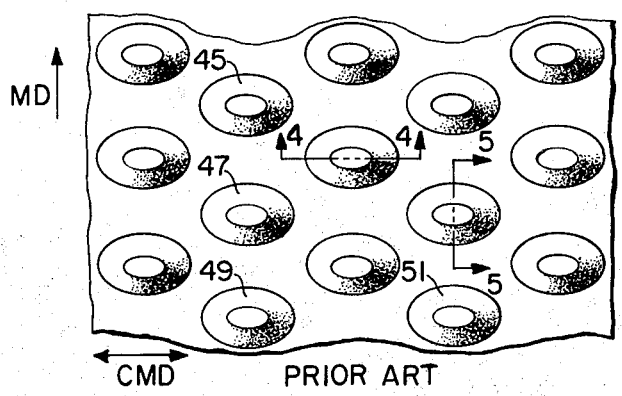
FIG. 3 is a plan view of the knobs of the prior art male embossing roll.
Figure 5:
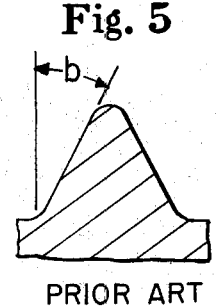
FIG. 5 is a sectional view of an embossing knob taken along line 5—5 of FIG. 3.

FIGS. 3, 4, and 5 show the arrangement and dimensions of the exterior portions of a prior art male embossing roll of a type which has been used commercially (oval pattern). In this prior art embodiment, the knobs are arranged in alternating staggered rows. The machine direction distance between the center of adjacent knobs such as 45 and 47 is 0.140 inches (3.56 mm.), and the cross-machine direction distance between the center of adjacent knobs such as 49 and 51 is 0.270 inches (6.86 mm.). The height of each knob is 0.070 inches (1.78 mm.), the length of the long axis of the land of each knob is 0.120 inches (3.05 mm.) in the cross-machine direction, and the length of the short axis of the land is 0.080 inches (2.03 mm.) in the machine direction. The land area of each knob is thus about 0.0075 square inches (4.84 mm.$^2$). The wall angle of the prior art knobs, represented by angle a in FIG. 4 and angle b in FIG. 5, is about 28 degrees. The radius of curvature at the base and tip of the prior art knob is about 0.025 inches (0.635 mm.).

Figure 6:
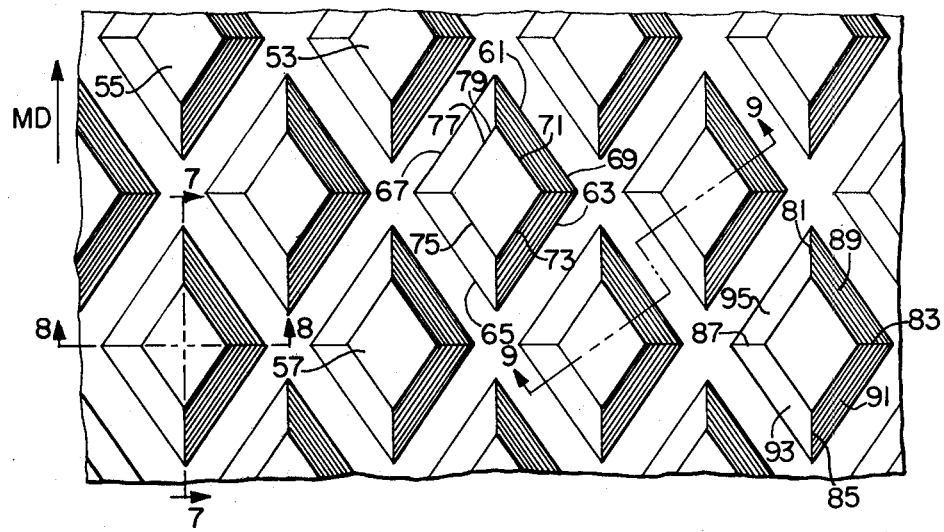
FIG. 6 is a plan view of the knobs of the male embossing roll of the present invention.
Figure 7:
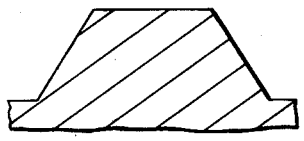
FIG. 7 is a sectional view taken alone line 7—7 of FIG. 6.
Figure 8:
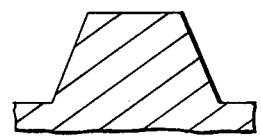
FIG. 8 is a sectional view taken along line 8—8 of FIG. 6.

FIGS. 6, 7, 8, and 9 illustrate the improved knob geometry of the present invention (diamond pattern). The cross-machine direction distance between the centers of adjacent knobs such as 53 and 55 in FIG. 6 is about 0.1434 inches (3.64 mm); the machine direction distance between the centers of adjacent knobs such as 53 and 57 is 0.2050 inches (5.21 mm). The knobs of the present development are each a frustum with a rhombic base and land, and the longer diagonal of each rhombus is aligned in the machine direction. The base has a longer diagonal of 0.1536 inches (3.90 mm) and a shorter diagonal of 0.1075 inches (2.73 mm.); the land of each knob has a longer diagonal of 0.082 inches (2.08 mm.) and a shorter diagonal of 0.0574 inches (1.458 mm.); the knob height is 0.060 inches (1.52 mm.). The land area of each knob is thus about 0.0024 square inches (1.55 mm.$^2$). Each rhombus has a smaller corner angle of about 70 degrees and a larger corner angle of about 110 degrees. Looking at FIG. 6 in greater detail (reference characters 61–95 of FIG. 6, relating to knob shape, are directed to more than one knob to clarify the illustration), base lines 61, 63, 65, and 67 define a base perimeter 69; land edges 71, 73, 75, and 77 define land perimeter 79; base perimeter 69 and land perimeter 79, in conjunction with leading edge 81, side edge 83, trailing edge 85, and side edge 87, define substantially planar side walls 89, 91, 93, and 95. Side walls 89, 91, 93, and 95 each define a plane angle c (shown in FIG. 9) of less than 28 degrees, and preferably about 20 degrees, with respect to plane which is perpendicular to base perimeter 69 and which contains the adjacent base line. In order to completely understand this depiction of the knob geometry of the present invention, it is necessary to note that section line 9—9 of FIG. 6 is perpendicular to the opposing base lines of the knobs it traverses.

Because the knobs such as 25 and depressions such as 27 of the mated embossing rolls are substantially identical in shape and size, it will be apparent that the above detailed description of the prior art and the present knob geometries is also a description of the depressions 27 of corresponding mated female embossing rolls 23 for each roll geometry. For this reason the dimensions of the depressions will not be set forth separately herein.

Figure 10:
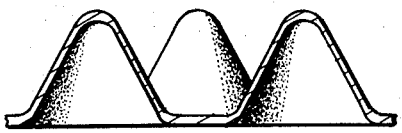
FIG. 10 is a side cutaway elevational view of a fragment of the embossed textile of the prior art.
Figure 11:
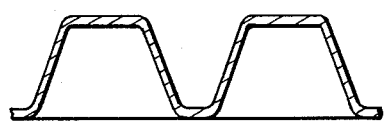
FIG. 11 is a side cutaway elevational view of a fragment of textile embossed in accordance with the present invention.

FIGS. 10 and 11 depict the pattern imparted to a textile by the prior art embossing rolls and by the present embossing rolls. It will be noted that the walls of the bosses of the present invention are more nearly perpendicular to the plane of the textile than are the side walls of the bosses produced using the prior art embossing pattern. Thus, the embossed textile of the present invention has a smaller side wall angle than is noted in embossed textiles of the prior art. (For purposes of this application the embossed textile side wall angle will be defined as the side wall angle of the embossing surfaces used to produce the textile, although it will be apparent to those skilled in the embossing art that the actual angles defined by the embossed textile will be greater than the corresponding side wall angles of the embossing tool as a result of resiliency of the material and of distortion resulting when the material is subjected to further handling and treatment.) Further, it will be noted that the bosses of the prior art textile are more rounded at their bases and apices than are the bosses of the textile of the present invention.

THE EMBOSSING ROLLS

The embossing rolls used to practice this invention are made of mild or of hardened steel in any of the ways known in the prior art. For example, to make the rolls used in the examples set forth hereinafter, a small male tooling roll is made in accordance with the geometry of a selected pattern. The face width and diameter of the tooling roll are a small fraction of the face width and diameter of the roll to be used in embossing. The tooling roll and a small portion of the blank roll which is to become the female roll are brought together to form a nip. The two rolls are then forced together and rotated in the presence of an acid bath to transfer a negative image of the pattern of the tooling roll to the female roll, in a manner which is well known in the art of making mating steel embossing rolls. This procedure is repeated sequentially for the several courses which must be engraved in the embossing roll with the tooling roll in order to cover the face of the embossing roll with the pattern of the tooling roll. This is done in such a way that the patterns of adjacent courses are in registration, so that the pattern is uniform across the face of the roll. In this manner the female roll is first completed.

The mated male embossing roll is produced in a similar way by rotating a blank roll with the finished female roll to form a nip, this time across the entire width of the blank roll. Pressure and an acid bath applied at the nip of the rotating rolls causes a negative image of the pattern of the female embossing roll to be impressed on the blank roll to form a male embossing roll. As a result of the use of the female embossing roll to engrave the male embossing roll, the two rolls have patterns which fit together very nearly completely, so that the pattern on the female roll is substantially the negative image of the pattern on the male embossing roll, and each pattern can be defined by a single surface which corresponds to the exterior dimensions of either roll. In this embodiment of the invention the roll diameters are each 8.02 inches (20.37 cm.).

In setting up the rolls to enable their use to emboss a textile sheet or web, the respective rolls are mounted in movable journals and adjusted so that the adjacent portions of the respective rolls are engaged, but with a minimum of about 0.002 inches (0.051 mm.) of roll clearance to avoid damaging the surfaces of the respective rolls when they are to be used for a substantial period of time. In the embodiment practiced by the present inventor, the male and female embossing rolls are each driven by means (not shown in the figures) connected to an axle at one end thereof, which means are adapted to rotate the rolls in synchronization to prevent opposed surfaces of mating knobs and depressions from contacting each other when the rolls are rotated. The rolls are rotated at a shaft speed of about 15 revolutions per minute, resulting in a roll surface speed of about 33 feet per minute (10.1 meters per minute).

The maximum roll clearance which may be used to practice the invention is not critical, except that when the male and female embossing rolls are so far separated that the distance therebetween approaches or exceeds the unembossed caliper of the textile used, little or no embossing will be noted. The optimum roll clearance is found to be about 0.004 inches (0.10 mm.) for a nonwoven textile with an unembossed caliper of about 0.008 inches (0.20 mm.). More generally, the optimum range of nip clearance for a textile with an unembossed caliper of 0.008 inches (0.20 mm.) is between 0.003 and 0.008 inches (0.076 mm. and 0.20 mm.). Where the unembossed caliper of the textile is greater than 0.008 inches (0.20 mm), the roll clearance may be increased accordingly in order to produce an optimal embossment.

It is well known in the embossing art that under certain circumstances it is desirable to heat the embossing rolls, the web to be embossed, or the like in order to improve the embossing operation by allowing greater flow of the embossed material. While such heating is not required in this embodiment of the invention, it will be apparent to those skilled in the art that heat could be applied at various points in the embossing apparatus without departing from the scope of the present invention.

MEASUREMENT OF SIDE WALL CLEARANCE

The side wall clearance between the corresponding knobs and depressions of mated embossing rolls is defined above as the perpendicular distance 39 between the respective side walls 41 and 43 of corresponding knob 25 and depression 27, as shown in FIG. 2.

Figure 9:
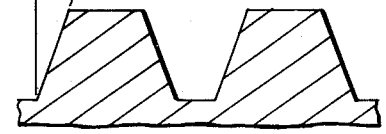
FIG. 9 is a sectional view taken along line 9—9 of FIG. 6, which crosses the respective bosses in a direction perpendicular to lines defining the edges of the bases thereof.

The side wall clearance can be calculated if the roll clearance 35 which separates depression floor 37 and knob land 38 is known, and if the wall angle between side wall 41 and a plane which is perpendicular to a plane containing boss perimeter 69 and which contains base line 42 is known. Thus, for the geometry of the present invention, the side wall clearance is given by the following equation:

$$SWC = RC (\sin c)$$

where SWC is side wall clearance, RC is roll clearance, and c is the side wall angle (shown in FIG. 9).

The side wall clearance of the prior art embossing pattern is calculated in essentially the same manner, except that the side wall angle is more easily defined because the side wall angle is constant around the entire perimeter of the knob or depression, so in FIGS. 4 and 5 angle a is equal to angle b. Thus, at any given point in the prior art pattern, the side wall clearance is again the sine of angle a (or angle b), multiplied by the roll clearance. Angle a is about 28 degrees and has a sine of 0.4695, while angle c is about 20 degrees, the sine of which is 0.3420.

For either of the above calculations, roll clearance is easily obtained by first adjusting the rolls to zero roll clearance, then measuring the difference between two reference points (such as the axles of the respective rolls), and then measuring the distance between the same reference points when the rolls are separated to a degree desired for a given embossing experiment.

CALIPER TEST

The tendency of embossed textiles to lose their embossed caliper, due to pressure applied in a direction which is perpendicular to the surface of the textile, is measured by determining the caliper of the textile at a pressure of 0.5 psi (0.35 g/mm.$^2$) using an Ames caliper gauge, Model 282JS, manufactured by B. C. Ames & Company, 131 Lexington Street, Waltham, Mass. 02154. (Of course, an equivalent gauge made by another manufacturer may be used to obtain essentially the same experimental results.) This particular gauge has a circular comparator foot made of aluminum and having a contact surface of 2 square inches (1290 mm.$^2$). The comparator base may be an Ames Model 16, 130, or 3 W base. The gauge is assembled according to B. C. Ames & Company Drawing No. 78-0.14.

EXAMPLE

For this example the textile selected was a polyester non-woven fabric sold under the trade name Cynthetex, manufactured by Stearns & Foster Cynthetex Corporation, Beaver Dam, Ky. This fabric is made of a polyester fiber material, having a mean fiber length of about 1.5 to about 1.56 inches (38 to 39.6 mm.) and a denier of 1.5, bonded with a National Starch vinyl acrylic latex denoted as Product No. 2833. This is a dry laid carded web which is bonded after carding. The wet tensile strengths of this fabric are about 2.2 lbs. per linear inch (393 g/lin. cm.) in the machine direction and about 0.34 lbs. per linear inch (61 g/lin. cm.) in the cross machine direction; its basis weight is about 0.42 lbs. per square yard (228 g/m.$^2$).

This textile was embossed at a variety of roll clearances. The side wall clearances were calculated from the roll clearances by multiplying the roll clearance by the sine of the side wall angle, and the high load caliper of each embossed sample was measured as explained above. This test was carried out for the prior art embossed pattern (oval pattern) and for the pattern used to practice the present invention (diamond pattern). Table 1 summarizes the results of these tests.

TABLE 1

| Roll Clearance | | Oval Pattern | | | | Diamond Pattern | | | |
| --- | --- | --- | --- | --- | --- | --- | --- | --- | --- |
| | | Side Wall Clearance | | High Load Caliper | | Side Wall Clearance | | High Load Caliper | |
| (in.) | (mm.) | (in.) | (mm.) | (in.) | (mm.) | (in.) | (mm.) | (in.) | (mm.) |
| .001 | .025 | .00047 | .0119 | .017 | .43 | .00034 | .0086 | .039 | .99 |
| .002 | .051 | .00094 | .0239 | .015 | .38 | .00068 | .0173 | .037 | .94 |
| .003 | .076 | .00141 | .0358 | .016 | .41 | .00103 | .0262 | .037 | .94 |
| .004 | .102 | .00188 | .0478 | .012 | .30 | .00137 | .0348 | .036 | .91 |
| .005 | .127 | .00235 | .0597 | .015 | .38 | .00171 | .0434 | .033 | .84 |
| .006 | .152 | .00282 | .0716 | .010 | .25 | .00205 | .0521 | .031 | .79 |
| .007 | .178 | .00329 | .0836 | .010 | .25 | .00239 | .0607 | .025 | .64 |
| .008 | .203 | .00376 | .0955 | .012 | .30 | .00274 | .0696 | .022 | .59 |
| .009 | .229 | .00423 | .1074 | .008 | .20 | .00308 | .0782 | .025 | .64 |
| .010 | .254 | .00469 | .1191 | .008 | .20 | .00342 | .0869 | .019 | .48 |

Figure 12:
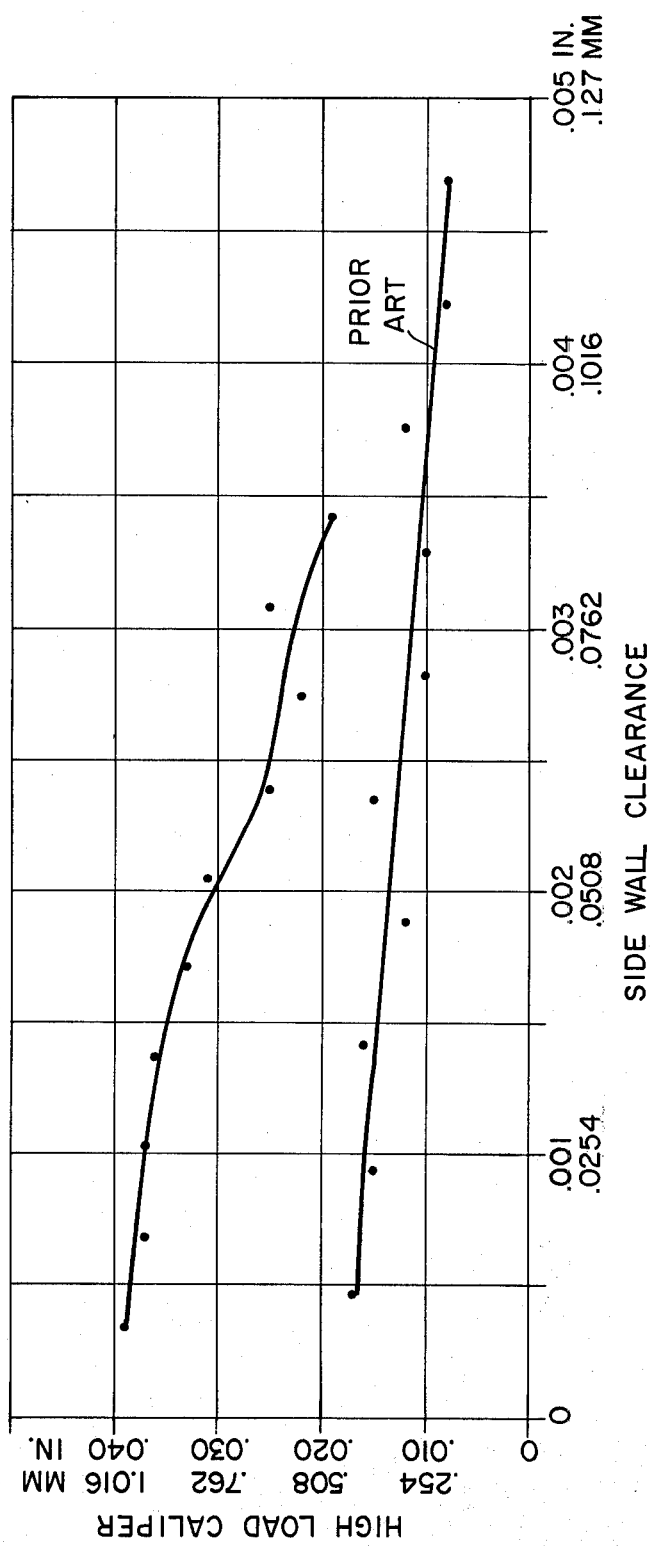
FIG. 12 is a graph which plots embossed textile caliper measured at 0.5 psi (0.35 g/mm.$^2$) pressure as a function of side wall clearance in the embossing apparatus; the prior art and present roll geometries are compared.

The high load (0.5 psi, 0.35 g/mm.$^2$) caliper for the embossed fabric is plotted with respect to side wall clearance for the respective patterns in the graph of FIG. 12. It will be noted from examining that graph, especially for a relatively low side wall clearance, that the upper line, which represents the caliper of material embossed according to the present invention, not only shows a greater embossed caliper at a given side wall clearance, but also displays a surprising sharp increase in high load caliper with a decrease in side wall clearance—this difference is much greater than that noted in the lower graph, which depicts the results using the prior art configuration, wherein only a slight rise in the embossed caliper is noted with a decrease in side wall clearance.

The inventor does not limit himself to any particular theory to explain the improvement of his embossing pattern over that of the prior art, although he believes that the following factors contribute. First, the lower side wall angle and increased angularity of the diamond embossing pattern tend to produce a sharply defined embossed pattern. Second, because the new pattern has a smaller side wall angle than does the prior art embossing pattern, the new pattern has a smaller side wall clearance for a given nip clearance so that the textile adjacent the side walls of the new embossing pattern is subjected to a higher degree of cold drawing than is observed in the textile embossed with the oval pattern. The inventor believes that this increase in cold drawing increases the tendency of individual molecles of the embossed material to align themselves in the direction in which the material is drawn, and thus to form a more highly crosslinked and coherent (i.e., more crystalline) molecular structure in the drawn portions of the textile. Another factor which increases the strength of textile embossed with the diamond pattern is that a boss having a lower side wall angle has columnar members which are more vertical, and which are thus more able to withstand a perpendicular force without crushing than is observed for prior art bosses. Finally, it will be noted from a comparison of FIG. 3 of the prior art and FIG. 6 depicting the improved geometry of the present invention that in the prior art embossing technique, the long axis of each knob is perpendicular to the machine direction, so that the nonwoven textile is first contacted by a relatively broad blunt face of each knob, while in the geometry of the present invention leading corner 81 and side walls 89 and 95 form a wedge which more gradually introduces the knob into the textile, even though (when the corresponding knob and depression are fully mated) the clearance between side walls 89, 91, 93, and 95 with respect to the corresponding depression walls is smaller than the side wall clearance noted in the prior art. Thus, the improved geometry of the present invention allows embossing with low side wall clearance, yet with less chance of localized tears or thin spots in individual bosses, which would tend to weaken the average boss wall strength.

It has been found that a nonwoven moisture-pervious textile which has been embossed in accordance with the present invention may be incorporated as an improved topsheet in a disposable diaper to more effectively present a dry outer surface to the wearer of the diaper than does a nonwoven topsheet which has been embossed in accordance with the prior art. Such a diaper is illustrated in FIG. 13 and described in the text hereinafter.

Figure 13:
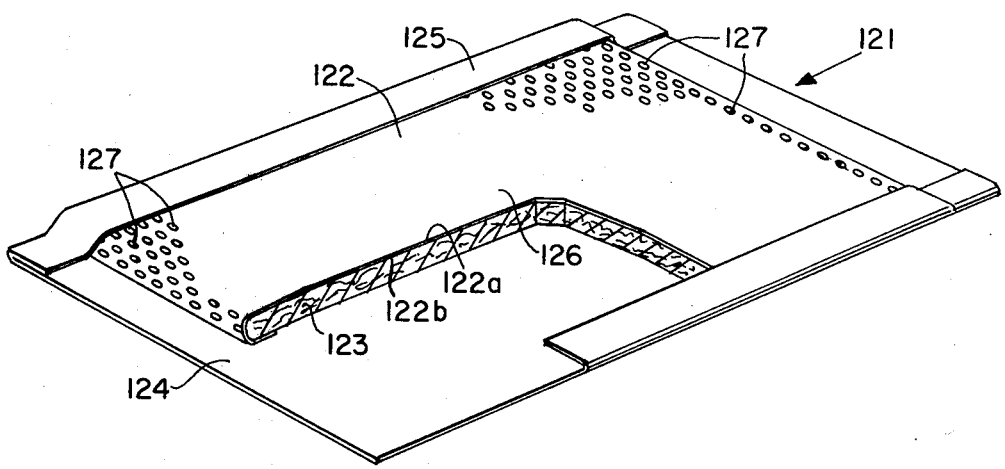
FIG. 13 is a perspective view of a disposable diaper which incorporates the improved embossed textile of the present invention, cut away to show the diaper internal structure.

FIG. 13 shows a disposable diaper in an unfolded condition. Various layers have been cut away to more clearly show the structural details of the particular embodiment. The disposable diaper is referred to generally by the reference 121. A novel topsheet of the present invention is shown at 122 having an uppermost surface 122a and a lower surface 122b. The other two major components of the disposable diaper 121 are the absorbent element or pad 123 and the backsheet 124. In general, the side flaps 125 of the backsheet 124 are folded so as to cover the edges of the absorbent pad 123 and topsheet 122. Topsheet 122 is generally folded to completely enclose the ends of absorbent pad 123. The drawing of diaper 121 in FIG. 13 is a simplified representation of a disposable diaper. A more detailed description of a preferred embodiment of a disposable diaper is contained in U.S. Pat. No. Re. 26,151 which issued to Duncan et al. on Jan. 31, 1967, and which is hereby incorporated herein by reference.

Absorbent pad 123 of the disposable diaper exemplified in FIG. 13 can comprise materials commonly used in absorptive devices and well known in the art. A preferred form of suitable absorbent material for use in the pad 123 is comminuted wood pulp generally referred to as air felt. When air felt is used, a tissue paper envelope, preferably comprised of wet strength tissue paper, is normally utilized to encapsulate the air felt and provide an absorbent pad 123 exhibiting satisfactory in-use integrity. Other materials can also be used for the absorbent pad 123, such as a multiplicity of plies of creped cellulose wadding or any equivalent thereof.

It is preferable that the uppermost surface of the absorbent pad 123 be substantially planar so as to avoid nesting of the absorbent material into intimate contact with the nondepressed areas 126 of the topsheet 122. Such nesting between the uppermost surface of the absorbent pad 123 and the nondepressed areas 126 of the moisture-previous topsheet 122 would obviously tend to minimize the physical isolation provided between the moist absorbent pad 123 and the nondepressed wearer-contacting surfaces 126 of the topsheet. Thus, the preferred areas of contact between the topsheet 122 and the uppermost surface of the absorbent pad 123 are limited, at least under a substantially no-load condition, to the bosses 127 of the topsheet.

Moisture-resistant backsheet 124 can be of any material well known in the art. A preferred material is a moisture-impervious, low-density polyethylene 0.001 to 0.002 inches (0.025 to 0.05 mm.) in thickness. If desired, a breathable, moisture-impervious backsheet containing apertured bosses, such as that described in Belgian Pat. No. 811,067 which issued to Sisson on Aug. 16, 1974, might also be employed.

The elements of a finished disposable diaper of the present invention—moisture-pervious generally hydrophobic topsheet 122, moisture-absorbent pad 123 and optional element such as moisture-impervious backsheet 124—can be assembled into a practical, economical disposable diaper by means well known in the art. An example of such union into disposable diapers is admirably described in U.S. Pat. No. Re. 26,151, which is incorporated by reference above.

As noted, the topsheet 122 containing bosses 127 and nondepressed areas 126 has been described in terms of disposable diapers. Other absorptive devices well known in the art such as sanitary napkins, catamenial tampons, bed pads, incontinent pads, towels, bandages, and the like can be advantageously constructed using a topsheet of the present invention. Specific examples of sanitary napkins and catamenial tampons wherein the topsheet of this invention can be used can be found in U.S. Pat. No. 3,800,797, issued to Tunc on Apr. 2, 1974, and U.S. Pat. No. 3,815,601, issued to Schaefer on June 11, 1974, both of which are hereby incorporated herein by reference.

I claim:

1. A disposable diaper comprising:
   means for absorbing moisture;
   a liquid impervious backsheet adjacent said means for absorbing moisture; and
   a topsheet adjacent said means for absorbing moisture oppositely disposed from said backsheet, said topsheet comprising a porous coherent nonwoven thermoplastic sheet with improved high loads caliper wherein said topsheet is a generally planar sheet having disposed thereon a multiplicity of elevated bosses having side walls and a land wherein said land and said side walls have a thickness no greater than the thickness of the unembossed sheet, said side walls define embossed side wall angles of less than 28 degrees to the perpendicular of said planar sheet.

2. The disposable diaper of claim 1 wherein said embossed side wall angles of said topsheet means are less than 20 degrees.

3. The disposable diaper of claim 2 wherein said topsheet means has bosses substantially defining the upper surface of a truncated pyramid with a rhombus-shaped base and land, and quadrangular, substantially planar side walls.

4. The disposable diaper of claim 3 wherein said topsheet comprises nonwoven, liquid-permeable thermoplastic material.

5. The disposable diaper of claim 4 wherein said topsheet comprises a multiplicity of elevated bosses having cold drawn side walls.

* * * * *

UNITED STATES PATENT AND TRADEMARK OFFICE
CERTIFICATE OF CORRECTION

PATENT NO. : 4,323,068
DATED : April 6, 1982
INVENTOR(S) : Mohammed I. Aziz

It is certified that error appears in the above-identified patent and that said Letters Patent are hereby corrected as shown below:

Column 6, line 41, "78-0.14" should read --78-014--.

Column 7, line 46, "molecles" should read --molecules--.

Column 10, line 10, "loads" should read --load--.

Signed and Sealed this

Twenty-fifth Day of June 1985

[SEAL]

Attest:

DONALD J. QUIGG

Attesting Officer

Acting Commissioner of Patents and Trademarks